(12) United States Patent
Dumble et al.

(10) Patent No.: US 9,402,846 B2
(45) Date of Patent: Aug. 2, 2016

(54) COMBINATION OF INHIBITOR OF B-RAF AND INHIBITOR OF AKT IN THE TREATMENT OF CANCER

(71) Applicant: Novartis AG, Basel (CH)

(72) Inventors: Melissa Dumble, Piscataway, NJ (US); Tona Gilmer, Research Triangle Park, NC (US); Rakesh Kumar, Collegeville, PA (US); Sylvie Laquerre, King of Prussia, PA (US); Peter F. Lebowitz, Collegeville, PA (US); Shannon Renae Morris, Research Triangle Park, NC (US)

(73) Assignee: Novartis AG, Basel (CH)

( * ) Notice: Subject to any disclaimer, the term of this patent is extended or adjusted under 35 U.S.C. 154(b) by 71 days.

(21) Appl. No.: 14/456,180

(22) Filed: Aug. 11, 2014

(65) Prior Publication Data

US 2014/0350039 A1 Nov. 27, 2014

Related U.S. Application Data

(62) Division of application No. 13/500,241, filed as application No. PCT/US2010/051907 on Oct. 8, 2010, now Pat. No. 8,835,450.

(60) Provisional application No. 61/249,803, filed on Oct. 8, 2009.

(51) Int. Cl.
| | |
|---|---|
| A61K 31/506 | (2006.01) |
| A61P 35/00 | (2006.01) |
| A61P 35/02 | (2006.01) |
| A61K 31/4155 | (2006.01) |
| A61K 45/06 | (2006.01) |

(52) U.S. Cl.
CPC ........... *A61K 31/506* (2013.01); *A61K 31/4155* (2013.01); *A61K 45/06* (2013.01)

(58) Field of Classification Search
CPC ........... A61K 2300/00; A61K 31/4155; A61K 31/506; A61K 45/06
See application file for complete search history.

(56) References Cited

U.S. PATENT DOCUMENTS

| 6,750,217 B2 | 6/2004 | Barrett et al. |
| 2005/0113423 A1 | 5/2005 | Van Goor et al. |

FOREIGN PATENT DOCUMENTS

| WO | WO2007/084391 | 7/2007 |
| WO | WO2008/098104 A1 | 8/2008 |
| WO | WO2008/098104 | 11/2008 |
| WO | WO 2009/137391 | 11/2009 |

OTHER PUBLICATIONS

Adams, et al., *Science*, 281:1322-1326 (1998).
Alessi, et al., *EMBO J.*, 15:6541-6551 (1996).
Babchia, et al., *Investigative Ophthalmology & Visual Science*, 51(1):421-429 (2010).
Bellacosa, et al., *Int. J. Cancer*, 64:280-285 (1995).
Chou, et al., *Advances in Enzyme Regulation*, 22:27-55 (1984).
Cohen, et al., *J. Nat. Cancer Inst.*, 95(8):625-627 (2003).
Crews, et al., *Cell*, 74:215-217 (1993).
Davies, et al., *Nature*, 417:949-954 (2002).
Downward, *Curr. Opin. Cell Biology*, 10:262-267 (1998).
Dudek, et al., *Science*, 275:661-665 (1997).
Franke, et al., *Cell*, 81:727-736 (1995).
Franke, et al., *Cell*, 88:435-437 (1997).
Guldberg et al. *Cancer Research* 57:3660-3663 (1997).
Hemmings, et al., *Science*, 275:628-630 (1997).
Hemmings, *Science*, 277:534 (1997).
J. Q. Cheung, et al., *Proc. Natl. Acad. Sci. USA*, 89:9267-9271 (1992).
J. Q. Cheung, et al., *Proc. Natl. Acad. Sci. USA*, 93:3636-3641 (1996).
Kauffmann-Zeh, et al., *Nature*, 385:544-548 (1997).
Kimura, et al., *Cancer Res.*, 63(7):1454-1454 (2003).
King, et al., *Cancer Res.*, 66:11100-11105 (2006).
Kulik, et al., *Mol. Cellular Biology*, 17:1595-1601 (1997).
Li et al. *Science* 275:1943-1947 (1997).
Liaw et al. *Nature Genetics* 16:64-67 (1997).
Liu, Q et al; Human Mutation 23:426-436 (2004).
Nakatani, et al., *J. Biol. Chem.*, 274:21528-21532 (1999).
Peterson, et al., *Frontiers Of Bioscience*, S2:483-503 (2010).
Peterson, et al., *Journal of Receptors and Signal Transduction*, 27(2-3):125-146 (2007).
Risinger et al. *Cancer Research* 57:4736-4738 (1997).
Stambolic et al. *Cell* 95:29-39 (1998).
Sun et al. *Proc. Nati. Acad. Sci. U.S.A.* 96:6199-6204 (1999).
Sun et al. *Am. J. Pathol.* 159: 431-7 (2001).
Thornberry, et al., *Science*, 281:1312-1316 (1998).
Tsail, et al., *PNAS*, 105(8):3041-3046 (2008); Abstract:3041-3043; 3046.
PCT/US2010/051907 International Search and Written Opinion.
Berenbaum, Morris C., "Criteria for Analyzing Interactions Between Biologically Active Agents", Advances in Cancer Research, vol. 35, pp. 269-335, 1981.
U.S. Appl. No. 61/148,490, filed Jan. 30, 2009.

*Primary Examiner* — Savitha Rao
(74) *Attorney, Agent, or Firm* — Michelle Han

(57) ABSTRACT

The present invention relates to a method of treating cancer in a human and to pharmaceutical combinations useful in such treatment. In particular, the method relates to a cancer treatment method that includes administering N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, to a human in need thereof.

15 Claims, No Drawings

COMBINATION OF INHIBITOR OF B-RAF AND INHIBITOR OF AKT IN THE TREATMENT OF CANCER

This application is a divisional of U.S. application Ser. No. 13/500,241, which is a National Stage filed on Apr. 4, 2012, which is a 371 of International Application No. PCT/US2010/051907 filed Oct. 8, 2010, which claims the benefit of U.S. Provisional Application No. 61/249,803 filed Oct. 8, 2009.

FIELD OF THE INVENTION

The present invention relates to a method of treating cancer in a mammal and to combinations useful in such treatment. In particular, the method relates to a novel combination comprising the B-Raf inhibitor: N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and the Akt inhibitor: N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, pharmaceutical compositions comprising the same, and methods of using such combinations in the treatment of cancer.

BACKGROUND OF THE INVENTION

Effective treatment of hyperproliferative disorders including cancer is a continuing goal in the oncology field. Generally, cancer results from the deregulation of the normal processes that control cell division, differentiation and apoptotic cell death. Apoptosis (programmed cell death) plays essential roles in embryonic development and pathogenesis of various diseases, such as degenerative neuronal diseases, cardiovascular diseases and cancer. One of the most commonly studied pathways, which involves kinase regulation of apoptosis, is cellular signaling from growth factor receptors at the cell surface to the nucleus (Crews and Erikson, Cell, 74:215-17, 1993).

An important large family of enzymes is the protein kinase enzyme family. There are about 500 different known protein kinases. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity including benign and malignant proliferative disorders as well as diseases resulting from inappropriate activation of the immune and nervous systems. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The protein serine/threonine kinases (PSTK), includes cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also in progress to identify modulators of tyrosine kinases as well.

Mitogen-activated protein (MAP) Kinase/extracellular signal-regulated kinase (ERK) kinase (hereinafter referred to as MEK) is known to be involved in the regulation of cell proliferation as a kinase that mediates Raf-MEK-ERK signal transduction pathway, and the Raf family (B-Raf, C-Raf etc.) activates the MEK family (MEK-1, MEK-2 etc.) and the MEK family activates the ERK family (ERK-1 and ERK-2).

Activation of Raf-MEK-ERK signal transduction pathway in cancer, particularly colorectal cancer, pancreatic cancer, lung cancer, breast cancer and the like, has been frequently observed.

Naturally occurring mutations of the B-Raf kinase that activate MAPK pathway signaling have been found in a large percentage of human melanomas (Davies (2002) supra) and thyroid cancers (Cohen et al *J. Nat. Cancer Inst.* (2003) 95(8) 625-627 and Kimura et al *Cancer Res.* (2003) 63(7) 1454-1457). By virtue of the role played by the Raf family kinases in these cancers and exploratory studies with a range of pre-clinical and therapeutic agents, including one selectively targeted to inhibition of B-Raf kinase activity (King A. J., et al., (2006) *Cancer Res.* 66:11100-11105), it is generally accepted that inhibitors of Raf family kinases will be useful for the treatment of such cancers or other condition associated with Raf kinase.

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-x$_L$, inhibits apoptotic cell death induced by various stimuli. On the other hand, expression of pro-apoptotic genes, such as Bax or Bad, leads to programmed cell death (Adams et al. *Science*, 281:1322-1326 (1998)). The execution of programmed cell death is mediated by caspase-1 related proteinases, including caspase-3, caspase-7, caspase-8 and caspase-9 etc (Thornberry et al. *Science*, 281:1312-1316 (1998)).

The phosphatidylinositol 3'-OH kinase (PI3K)/Akt/PKB pathway appears important for regulating cell survival/cell death (Kulik et al. *Mol. Cell. Biol.* 17:1595-1606 (1997); Franke et al, *Cell,* 88:435-437 (1997); Kauffmann-Zeh et al. *Nature* 385:544-548 (1997) Hemmings *Science,* 275:628-630 (1997); Dudek et al., *Science,* 275:661-665 (1997)). Survival factors, such as platelet derived growth factor (PDGF), nerve growth factor (NGF) and insulin-like growth factor-1 (IGF-I), promote cell survival under various conditions by inducing the activity of PI3K (Kulik et al. 1997, Hemmings 1997). Activated PI3K leads to the production of phosphatidylinositol (3,4,5)-triphosphate (PtdIns (3,4,5)-P3), which in turn binds to, and promotes the activation of, the serine/threonine kinase Akt, which contains a pleckstrin homology (PH)-domain (Franke et al *Cell,* 81:727-736 (1995); Hemmings *Science,* 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmannin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267-9271 (1992)) and pancreatic cancers (J. Q. Cheung et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999). It was demonstrated that Akt-2 was over-expressed in 12% of ovarian carcinomas and that amplification of Akt was especially frequent in 50% of undifferentiated tumors, suggestion that Akt may also be associated with tumor aggressiveness (Bellacosa, et al., *Int. J. Cancer,* 64, pp. 280-285, 1995). Increased Akt1 kinase activity has been reported in breast, ovarian and prostate cancers (Sun et al. *Am. J. Pathol.* 159: 431-7 (2001)).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis and/or cancer.

It would be useful to provide a novel therapy which provides more effective and/or enhanced treatment of an individual suffering the effects of cancer.

SUMMARY OF THE INVENTION

One embodiment of this invention provides a combination comprising:

(i) a compound of Structure (I):

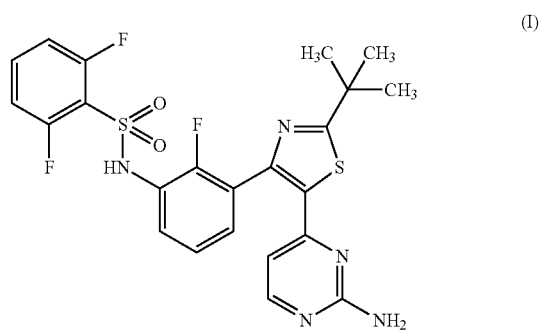 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof; and
(ii) a compound of Structure (II):

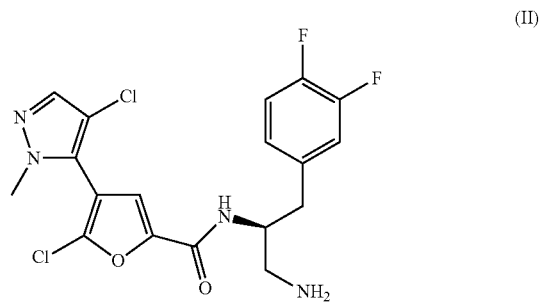 [SMILES: Cn1ncc(Cl)c1-c1cc(C(=O)N[C@H](CN)Cc2ccc(F)c(F)c2)oc1Cl]

or a pharmaceutically acceptable salt thereof.

One embodiment of this invention provides a method of treating cancer in a human in need thereof which comprises the in vivo administration of a therapeutically effective amount of a combination of N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt, suitably the methanesulfonate salt, thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, to such human.

One embodiment of this invention provides a method of treating cancer in a human in need thereof which comprises the in vivo administration of a therapeutically effective amount of a combination of N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt, suitably the methanesulfonate salt, thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, to such human,
  wherein the combination is administered within a specified period, and
  wherein the combination is administered for a duration of time.

One embodiment of this invention provides a method of treating cancer in a human in need thereof which comprises the in vivo administration of a therapeutically effective amount of a combination of N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt, suitably the methanesulfonate salt, thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, to such human,
wherein the compounds of the combination are administered sequentially.

DETAILED DESCRIPTION OF THE INVENTION

The present invention relates to combinations that exhibit antiproliferative activity. Suitably, the method relates to methods of treating cancer by the co-administration of N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt, suitably the methanesulfonate salt, thereof, (hereinafter Compound A, or a pharmaceutically acceptable salt, suitably the methanesulfonate salt, thereof,
which compound is represented by Structure I:

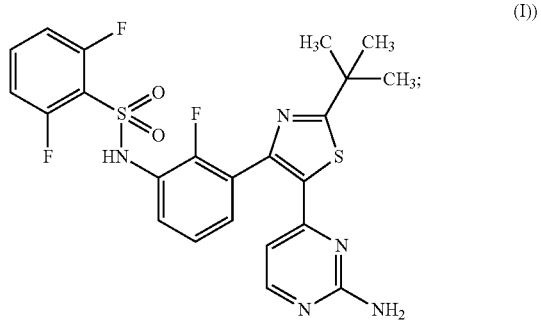 [SMILES: CC(C)(C)c1nc(-c2cccc(NS(=O)(=O)c3c(F)cccc3F)c2F)c(-c2ccnc(N)n2)s1]

and N-{(1S)-2-amino-1-[(3,4-difluorophenyl)methyl]ethyl}-5-chloro-4-(4-chloro-1-methyl-1H-pyrazol-5-yl)-2-furancarboxamide or a pharmaceutically acceptable salt thereof, (hereinafter Compound B or a pharmaceutically acceptable salt thereof,
which compound is represented by Structure II:

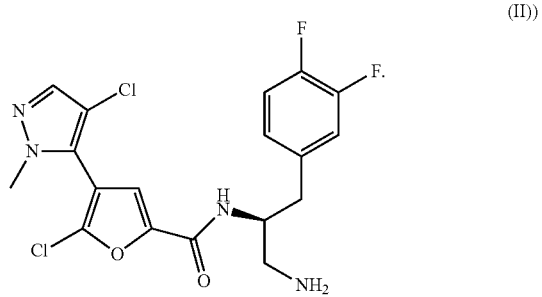 [SMILES: Cn1ncc(Cl)c1-c1cc(C(=O)N[C@H](CN)Cc2ccc(F)c(F)c2)oc1Cl]

Compound A is disclosed and claimed, along with pharmaceutically acceptable salts thereof, as being useful as an inhibitor of B-Raf activity, particularly in treatment of cancer, in International Application No. PCT/US2009/042682, having an International filing date of May 4, 2009, International Publication Number WO 2009/137391 and an International Publication date of Nov. 12, 2009, the entire disclosure of which is hereby incorporated by reference, Compound A is the compound of Example 58. Compound A can be prepared as described in International Application No. PCT/US2009/042682.

Suitably, Compound A is in the form of a methanesulfonate salt. This salt form can be prepared by one of skill in the art from the description in International Application No. PCT/US2009/042682, having an International filing date of May 4, 2009.

Compound B is disclosed and claimed, along with pharmaceutically acceptable salts thereof, as being useful as an inhibitor of AKT activity, particularly in treatment of cancer, in International Application No. PCT/US2008/053269, having an International filing date of Feb. 7, 2008; International Publication Number WO 2008/098104 and an International Publication date of Aug. 14, 2008, the entire disclosure of which is hereby incorporated by reference, Compound B is the compound of example 224. Compound B can be prepared as described in International Application No. PCT/US2008/053269.

The administration of a therapeutically effective amount of the combinations of the invention are advantageous over the individual component compounds in that the combinations will provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the component compounds.

The compounds of the invention may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of Compound A, and pharmaceutically acceptable salts thereof, and Compound B, and pharmaceutically acceptable salts thereof.

The compounds of the invention may form a solvate which is understood to be a complex of variable stoichiometry formed by a solute (in this invention, Compound A or a salt thereof and/or Compound B or a salt thereof) and a solvent. Such solvents for the purpose of the invention may not interfere with the biological activity of the solute. Examples of suitable solvents include, but are not limited to, water, methanol, dimethyl sulfoxide, ethanol and acetic acid. Suitably the solvent used is a pharmaceutically acceptable solvent. Suitably the solvent used is water.

The pharmaceutically acceptable salts of the compounds of the invention are readily prepared by those of skill in the art.

Also, contemplated herein is a method of treating cancer using a combination of the invention where Compound A, or a pharmaceutically acceptable salt thereof, and/or Compound B or a pharmaceutically acceptable salt thereof are administered as pro-drugs. Pharmaceutically acceptable pro-drugs of the compounds of the invention are readily prepared by those of skill in the art.

When referring to a dosing protocol, the term "day", "per day" and the like, refer to a time within one calendar day which begins at midnight and ends at the following midnight.

By the term "treating" and derivatives thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

By the term "combination" and derivatives thereof, as used herein is meant either simultaneous administration or any manner of separate sequential administration of a therapeutically effective amount of Compound A, or a pharmaceutically acceptable salt thereof, and Compound B or a pharmaceutically acceptable salt thereof. Preferably, if the administration is not simultaneous, the compounds are administered in a close time proximity to each other. Furthermore, it does not matter if the compounds are administered in the same dosage form, e.g. one compound may be administered topically and the other compound may be administered orally. Suitably, both compounds are administered orally.

By the term "combination kit" as used herein is meant the pharmaceutical composition or compositions that are used to administer Compound A, or a pharmaceutically acceptable salt thereof, and Compound B, or a pharmaceutically acceptable salt thereof, according to the invention. When both compounds are administered simultaneously, the combination kit can contain Compound A, or a pharmaceutically acceptable salt thereof, and Compound B, or a pharmaceutically acceptable salt thereof, in a single pharmaceutical composition, such as a tablet, or in separate pharmaceutical compositions. When the compounds are not administered simultaneously, the combination kit will contain Compound A, or a pharmaceutically acceptable salt thereof, and Compound B, or a pharmaceutically acceptable salt thereof, in separate pharmaceutical compositions. The combination kit can comprise Compound A, or a pharmaceutically acceptable salt thereof, and Compound B, or a pharmaceutically acceptable salt thereof, in separate pharmaceutical compositions in a single package or in separate pharmaceutical compositions in separate packages.

In one aspect there is provided a combination kit comprising the components:

Compound A, or a pharmaceutically acceptable salt thereof, in association with a pharmaceutically acceptable carrier; and Compound B, or a pharmaceutically acceptable salt thereof, in association with a pharmaceutically acceptable carrier.

In one embodiment of the invention the combination kit comprises the following components:

Compound A, or a pharmaceutically acceptable salt thereof, in association with a pharmaceutically acceptable carrier; and Compound B, or a pharmaceutically acceptable salt thereof, in association with a pharmaceutically acceptable carrier, wherein the components are provided in a form which is suitable for sequential, separate and/or simultaneous administration.

In one embodiment the combination kit comprises:

a first container comprising Compound A, or a pharmaceutically acceptable salt thereof, in association with a pharmaceutically acceptable carrier; and a second container comprising Compound B, or a pharmaceutically acceptable salt thereof, in association with a pharmaceutically acceptable carrier, and a container means for containing said first and second containers.

The "combination kit" can also be provided by instruction, such as dosage and administration instructions. Such dosage and administration instructions can be of the kind that is provided to a doctor, for example by a drug product label, or they can be of the kind that is provided by a doctor, such as instructions to a patient.

Unless otherwise defined, in all dosing protocols described herein, the regimen of compounds administered does not have to commence with the start of treatment and terminate with the end of treatment, it is only required that the number of consecutive days in which both compounds are administered and the optional number of consecutive days in which only one of the component compounds is administered, or the indicated dosing protocol—including the amount of compound administered, occur at some point during the course of treatment.

As used herein the term "Compound $A^2$" means—Compound A, or a pharmaceutically acceptable salt thereof—.

As used herein the term "Compound $B^2$" means—Compound B, or a pharmaceutically acceptable salt thereof—.

The term "loading dose" as used herein will be understood to mean a single dose or short duration regimen of Compound A or Compound B having a dosage higher than the maintenance dose administered to the subject to, for example, rapidly increase the blood concentration level of the drug. Suitably, a short duration regimen for use herein will be from: 1 to 14 days; suitably from 1 to 7 days; suitably from 1 to 3 days; suitably for three days; suitably for two days; suitably for one day. In some embodiments, the "loading dose" can increase the blood concentration of the drug to a therapeutically effective level. In some embodiments, the "loading dose" can increase the blood concentration of the drug to a therapeutically effective level in conjunction with a maintenance dose of the drug. The "loading dose" can be administered once per day, or more than once per day (e.g., up to 4 times per day). Suitably the "loading dose" will be administered once a day. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading dose will be administered for from 1 to 7 days; suitably from 1 to 5 days; suitably from 1 to 3 days; suitably for 1 day; suitably for 2 days; suitably for 3 days, followed by a maintenance dosing protocol.

The term "maintenance dose" as used herein will be understood to mean a dose that is serially administered (for example; at least twice), and which is intended to either slowly raise blood concentration levels of the compound to a therapeutically effective level, or to maintain such a therapeutically effective level. The maintenance dose is generally administered once per day and the daily dose of the maintenance dose is lower than the total daily dose of the loading dose.

Suitably the combinations of this invention are administered within a "specified period".

By the term "specified period" and derivatives thereof, as used herein is meant the interval of time between the administration of one of Compound $A^2$ and Compound $B^2$ and the other of Compound $A^2$ and Compound $B^2$. Unless otherwise defined, the specified period can include simultaneous administration. When both compounds of the invention are administered once a day the specified period refers to the timing of the administration of Compound $A^2$ and Compound $B^2$ during a single day. When one or both compounds of the invention are administered more than once a day, the specified period is calculated based on the first administration of each compound on a specific day. All administrations of a compound of the invention that are subsequent to the first during a specific day are not considered when calculating the specific period.

Suitably, if the compounds are administered within a "specified period" and not administered simultaneously, they are both administered within about 24 hours of each other—in this case, the specified period will be about 24 hours; suitably they will both be administered within about 12 hours of each other—in this case, the specified period will be about 12 hours; suitably they will both be administered within about 11 hours of each other—in this case, the specified period will be about 11 hours; suitably they will both be administered within about 10 hours of each other—in this case, the specified period will be about 10 hours; suitably they will both be administered within about 9 hours of each other—in this case, the specified period will be about 9 hours; suitably they will both be administered within about 8 hours of each other—in this case, the specified period will be about 8 hours; suitably they will both be administered within about 7 hours of each other—in this case, the specified period will be about 7 hours; suitably they will both be administered within about 6 hours of each other—in this case, the specified period will be about 6 hours; suitably they will both be administered within about 5 hours of each other—in this case, the specified period will be about 5 hours; suitably they will both be administered within about 4 hours of each other—in this case, the specified period will be about 4 hours; suitably they will both be administered within about 3 hours of each other—in this case, the specified period will be about 3 hours; suitably they will be administered within about 2 hours of each other—in this case, the specified period will be about 2 hours; suitably they will both be administered within about 1 hour of each other—in this case, the specified period will be about 1 hour. As used herein, the administration of Compound $A^2$ and Compound $B^2$ in less than about 45 minutes apart is considered simultaneous administration.

Suitably, when the combination of the invention is administered for a "specified period", the compounds will be co-administered for a "duration of time".

By the term "duration of time" and derivatives thereof, as used herein is meant that both compounds of the invention are administered within a "specified period" for an indicated number of consecutive days, optionally followed by a number of consecutive days where only one of the component compounds is administered.

Regarding "specified period" administration:

Suitably, both compounds will be administered within a specified period for at least one day—in this case, the duration of time will be at least one day; suitably, during the course to treatment, both compounds will be administered within a specified period for at least 3 consecutive days—in this case, the duration of time will be at least 3 days; suitably, during the course to treatment, both compounds will be administered within a specified period for at least 5 consecutive days—in this case, the duration of time will be at least 5 days; suitably, during the course to treatment, both compounds will be administered within a specified period for at least 7 consecutive days—in this case, the duration of time will be at least 7 days; suitably, during the course to treatment, both compounds will be administered within a specified period for at least 14 consecutive days—in this case, the duration of time will be at least 14 days; suitably, during the course to treatment, both compounds will be administered within a specified period for at least 30 consecutive days—in this case, the duration of time will be at least 30 days.

Suitably, during the course of treatment, both compounds will be administered within a specified period for at least 1 day—in this case, the duration of time will be at least 1 day; suitably, during the course of treatment, both compounds will be administered within a specified period for at least 2 consecutive days—in this case, the duration of time will be at least 2 days; suitably, during the course of treatment, both compounds will be administered within a specified period for at least 3 consecutive days—in this case, the duration of time will be at least 3 days; suitably, during the course of treatment, both compounds will be administered within a specified period for at least 5 consecutive days —in this case, the duration of time will be at least 5 days; suitably, during the course of treatment, both compounds will be administered within a specified period for at least 7 consecutive days—in this case, the duration of time will be at least 7 days; suitably, during the course of treatment, both compounds will be administered within a specified period for at least 14 consecutive days—in this case, the duration of time will be at least 14 days; suitably, during the course of treatment, both compounds will be administered within a specified period for at least 30 consecutive days—in this case, the duration of time will be at least 30 days. When, during the course of treatment, both compounds are administered within a specified period for over 30 days, the treatment is considered chronic treatment and will continue until an altering event, such as a reassessment in cancer status or a change in the condition of the patient, warrants a modification to the protocol.

Further regarding "specified period" administration:

Suitably, during the course of treatment, both compounds will be administered within a specified period for at least 1 day, followed by the administration of Compound $A^2$ alone for at least 1 day—in this case, the duration of time will be at least 2 days; suitably, during the course of treatment, both compounds will be administered within a specified period for at least 1 day, followed by administration of Compound $A^2$ alone for at least 2 days—in this case, the duration of time will be at least 3 days; suitably, during the course of treatment, both compounds will be administered within a specified period for at least 1 day, followed by administration of Compound $A^2$ alone for at least 3 days—in this case, the duration of time will be at least 4 days; suitably, during the course of treatment, both compounds will be administered within a specified period for at least 1 day, followed by administration of Compound $A^2$ alone for at least 4 days—in this case, the duration of time will be at least 5 days; suitably, during the course of treatment, both compounds will be administered within a specified period for at least 1 day, followed by administration of Compound $A^2$ alone for at least 5 days—in this case, the duration of time will be at least 6 days; suitably, during the course of treatment, both compounds will be administered within a specified period for at least 1 day, followed by administration of Compound $A^2$ alone for at least 6 days—in this case, the duration of time will be at least 7 days; suitably, during the course of treatment, both compounds will be administered within a specified period for at least 1 day, followed by administration of Compound $A^2$ alone for at least 7 days—in this case, the duration of time will be at least 8 days; suitably, during the course of treatment, both compounds will be administered within a specified period for at least 2 consecutive days, followed by administration of Compound $A^2$ alone for at least 1 day—in this case, the duration of time will be at least 3 days; suitably, during the course of treatment, both compounds will be administered within a specified period for at least 2 consecutive days, followed by administration of Compound $A^2$ alone for at least 2 consecutive days—in this case, the duration of time will be at least 4 days; suitably, during the course of treatment, both compounds will be administered within a specified period for at least 2 consecutive days, followed by administration of Compound $A^2$ alone for at least 3 consecutive days—in this case, the duration of time will be at least 5 days; suitably, during the course of treatment, both compounds will be administered within a specified period for at least 2 consecutive days, followed by administration of Compound $A^2$ alone for at least 4 consecutive days—in this case, the duration of time will be at least 6 days; suitably, during the course of treatment, both compounds will be administered within a specified period for at least 2 consecutive days, followed by administration of Compound $A^2$ alone for at least 5 consecutive days—in this case, the duration of time will be at least 7 days; suitably, during the course of treatment, both compounds will be administered within a specified period for at least 2 consecutive days, followed by administration of Compound $A^2$ alone for at least 6 consecutive days—in this case, the duration of time will be at least 8 days; suitably, during the course of treatment, both compounds will be administered within a specified period for at least 2 consecutive days, followed by administration of Compound $A^2$ alone for at least 7 consecutive days—in this case, the duration of time will be at least 9 days; suitably, during the course of treatment, both compounds will be administered within a specified period for at least 3 consecutive days, followed by administration of Compound $A^2$ alone for at least 1 day—in this case, the duration of time will be at least 4 days; suitably, during the course of treatment, both compounds will be administered within a specified period for at least 3 consecutive days, followed by administration of Compound $A^2$ alone for at least 2 consecutive days—in this case, the duration of time will be at least 5 days; suitably, during the course of treatment, both compounds will be administered within a specified period for at least 3 consecutive days, followed by administration of Compound $A^2$ alone for at least 3 consecutive days—in this case, the duration of time will be at least 6 days; suitably, during the course of treatment, both compounds will be administered within a specified period for at least 3 consecutive days, followed by administration of Compound $A^2$ alone for at least 4 consecutive days—in this case, the duration of time will be at least 7 days; suitably, during the course of treatment, both compounds will be administered within a specified period for at least 3 consecutive days, followed by administration of Compound $A^2$ alone for at least 5 consecutive days—in this case, the duration of time will be at least 8 days; suitably, during the course of treatment, both compounds will be administered within a specified period for at least 3 consecutive days, followed by administration of Compound $A^2$ alone for at least 6 consecutive days—in this case, the duration of time will be at least 9 days; suitably, during the course of treatment, both compounds will be administered within a specified period for at least 3 consecutive days, followed by administration of Compound $A^2$ alone for at least 7 consecutive days—in this case, the duration of time will be at least 10 days; suitably, during the course of treatment, both compounds will be administered within a specified period for at least 4 consecutive days, followed by administration of Compound $A^2$ alone for at least 1 day—in this case, the duration of time will be at least 5 consecutive days; suitably, during the course of treatment, both compounds will be administered within a specified period for at least 4 consecutive days, followed by administration of Compound $A^2$ alone for at least 2 consecutive days—in this case, the duration of time will be at least 6 consecutive days; suitably, during the course of treatment, both compounds will be administered within a specified period for at least 4 consecutive days, followed by administration of Compound $A^2$ alone for at least 3 consecutive days—in this case, the duration of time will be at least 7 consecutive days; suitably, during the course of treatment, both compounds will be administered within a specified period for at least 4 consecutive days, followed by administration of Compound $A^2$ alone for at least 4 consecutive days—in this case, the duration of time will be at least 8 consecutive days; suitably, during the course of treatment, both compounds will be administered within a specified period for at least 4 consecutive days, followed by administration of Compound $A^2$ alone for at least 7 consecutive days—in this case, the duration of time will be at least 11 consecutive days; suitably, during the course of treatment, both compounds will be administered within a specified period for at least 5 consecutive days, followed by administration of Compound $A^2$ alone for at least 1 day—in this case, the duration of time will be at least 6 consecutive days; suitably, during the course of treatment, both compounds will be administered within a specified period for at least 5 consecutive days, followed by administration of Compound $A^2$ alone for at least 2 consecutive days—in this case, the duration of time will be at least 7 consecutive days; suitably, during the course of treatment, both compounds will be administered within a specified period for at least 5 consecutive days, followed by administration of Compound $A^2$ alone for at least 3 consecutive days—in this case, the duration of time will be at least 8 consecutive days; suitably, during the course of treatment, both compounds will be administered within a specified period for at least 5 consecutive days, followed by administration of Compound $A^2$ alone for at least 4 consecutive days—in this case, the duration of time will be at least 9 consecutive days; suitably, during the course of treatment, both compounds will be administered within a specified period for at least 5 consecutive days, followed by administration of Compound $A^2$ alone for at least 5 consecutive days—in this case, the duration of time will be at least 10 consecutive days; suitably, during the course of treatment, both compounds will be administered within a specified period for at least 7 consecutive days, followed by administration of Compound $A^2$ alone for at least 2 consecutive days—in this case, the duration of time will be at least consecutive days; suitably, during the course of treatment, both compounds will be administered within a specified period for at least 14 consecutive days, followed by administration of Compound $A^2$ alone for at least 7 consecutive days—in this case, the duration of time will be at least 21 consecutive days; suitably, during the course of treatment, both compounds will be administered within a specified period for at least 30 consecutive days, followed by administration of Compound $A^2$ alone for at least 7 consecutive days—in this case, the duration of time will be at least 37 consecutive days. Suitably, during the course of treatment, both compounds will be administered within a specified period for from 1 to 3 consecutive days, followed by administration of Compound $A^2$ alone for from 3 to 7 consecutive days. Suitably, during the course of treatment, both compounds will be administered within a specified period for from 3 to 6 consecutive days, followed by administration of Compound $A^2$ alone for from 1 to 4 consecutive days. Suitably, during the course of treatment, both compounds will be administered within a specified period for 5 consecutive days, followed by administration of Compound $A^2$ alone for 2 consecutive days. Suitably, during the course of treatment, both compounds will be administered within a specified period for 2 consecutive days, followed by administration of Compound $A^2$ alone for from 3 to 7 consecutive days.

Further regarding "specified period" administration:

Suitably, during the course of treatment, both compounds will be administered within a specified period for at least 1 day, followed by the administration of Compound $B^2$ alone for at least 1 day—in this case, the duration of time will be at least 2 days; suitably, during the course of treatment, both compounds will be administered within a specified period for at least 1 day, followed by administration of Compound $B^2$ alone for at least 2 days—in this case, the duration of time will be at least 3 days; suitably, during the course of treatment, both compounds will be administered within a specified period for at least 1 day, followed by administration of Compound $B^2$ alone for at least 3 days—in this case, the duration of time will be at least 4 days; suitably, during the course of treatment, both compounds will be administered within a specified period for at least 1 day, followed by administration of Compound $B^2$ alone for at least 4 days—in this case, the duration of time will be at least 5 days; suitably, during the course of treatment, both compounds will be administered within a specified period for at least 1 day, followed by administration of Compound $B^2$ alone for at least 5 days—in this case, the duration of time will be at least 6 days; suitably, during the course of treatment, both compounds will be administered within a specified period for at least 1 day, followed by administration of Compound $B^2$ alone for at least 6 days—in this case, the duration of time will be at least 7 days; suitably, during the course of treatment, both compounds will be administered within a specified period for at least 1 day, followed by administration of Compound $B^2$ alone for at least 7 days—in this case, the duration of time will be at least 8 days; suitably, during the course of treatment, both compounds will be administered within a specified period for at least 2 consecutive days, followed by administration of Compound $B^2$ alone for at least 1 day—in this case, the duration of time will be at least 3 days; suitably, during the course of treatment, both compounds will be administered within a specified period for at least 2 consecutive days, followed by administration of Compound $B^2$ alone for at least 2 consecutive days—in this case, the duration of time will be at least 4 days; suitably, during the course of treatment, both compounds will be administered within a specified period for at least 2 consecutive days, followed by administration of Compound $B^2$ alone for at least 3 consecutive days—in this case, the duration of time will be at least 5 days; suitably, during the course of treatment, both compounds will be administered within a specified period for at least 2 consecutive days, followed by administration of Compound $B^2$ alone for at least 4 consecutive days—in this case, the duration of time will be at least 6 days; suitably, during the course of treatment, both compounds will be administered within a specified period for at least 2 consecutive days, followed by administration of Compound $B^2$ alone for at least 5 consecutive days—in this case, the duration of time will be at least 7 days; suitably, during the course of treatment, both compounds will be administered within a specified period for at least 2 consecutive days, followed by administration of Compound $B^2$ alone for at least 6 consecutive days—in this case, the duration of time will be at least 8 days; suitably, during the course of treatment, both compounds will be administered within a specified period for at least 2 consecutive days, followed by administration of Compound $B^2$ alone for at least 7 consecutive days—in this case, the duration of time will be at least 9 days; suitably, during the course of treatment, both compounds will be administered within a specified period for at least 3 consecutive days, followed by administration of Compound $B^2$ alone for at least 1 day—in this case, the duration of time will be at least 4 days; suitably, during the course of treatment, both compounds will be administered within a specified period for at least 3 consecutive days, followed by administration of Compound $B^2$ alone for at least 2 consecutive days—in this case, the duration of time will be at least 5 days; suitably, during the course of treatment, both compounds will be administered within a specified period for at least 3 consecutive days, followed by administration of Compound $B^2$ alone for at least 3 consecutive days—in this case, the duration of time will be at least 6 days; suitably, during the course of treatment, both compounds will be administered within a specified period for at least 3 consecutive days, followed by administration of Compound $B^2$ alone for at least 4 consecutive days—in this case, the duration of time will be at least 7 days; suitably, during the course of treatment, both compounds will be administered within a specified period for at least 3 consecutive days, followed by administration of Compound $B^2$ alone for at least 5 consecutive days—in this case, the duration of time will be at least 8 days; suitably, during the course of treatment, both compounds will be administered within a specified period for at least 3 consecutive days, followed by administration of Compound $B^2$ alone for at least 6 consecutive days—in this case, the duration of time will be at least 9 days; suitably, during the course of treatment, both compounds will be administered within a specified period for at least 3 consecutive days, followed by administration of Compound $B^2$ alone for at least 7 consecutive days—in this case, the duration of time will be at least 10 days; suitably, during the course of treatment, both compounds will be administered within a specified period for at least 4 consecutive days, followed by administration of Compound $B^2$ alone for at least 1 day—in this case, the duration of time will be at least 5 consecutive days; suitably, during the course of treatment, both compounds will be administered within a specified period for at least 4 consecutive days, followed by administration of Compound $B^2$ alone for at least 2 consecutive days—in this case, the duration of time will be at least 6 consecutive days; suitably, during the course of treatment, both compounds will be administered within a specified period for at least 4 consecutive days, followed by administration of Compound $B^2$ alone for at least 3 consecutive days—in this case, the duration of time will be at least 7 consecutive days; suitably, during the course of treatment, both compounds will be administered within a specified period for at least 4 consecutive days, followed by administration of Compound $B^2$ alone for at least 4 consecutive days—in this case, the duration of time will be at least 8 consecutive days; suitably, during the course of treatment, both compounds will be administered within a specified period for at least 4 consecutive days, followed by administration of Compound $B^2$ alone for at least 7 consecutive days—in this case, the duration of time will be at least 11 consecutive days; suitably, during the course of treatment, both compounds will be administered within a specified period for at least 5 consecutive days, followed by administration of Compound $B^2$ alone for at least 1 day—in this case, the duration of time will be at least 6 consecutive days; suitably, during the course of treatment, both compounds will be administered within a specified period for at least 5 consecutive days, followed by administration of Compound $B^2$ alone for at least 2 consecutive days—in this case, the duration of time will be at least 7 consecutive days; suitably, during the course of treatment, both compounds will be administered within a specified period for at least 5 consecutive days, followed by administration of Compound $B^2$ alone for at least 3 consecutive days—in this case, the duration of time will be at least 8 consecutive days; suitably, during the course of treatment, both compounds will be administered within a specified period for at least 5 consecutive days, followed by administration of Compound $B^2$ alone for at least 4 consecutive days—in this case, the duration of time will be at least 9 consecutive days; suitably, during the course of treatment, both compounds will be administered within a specified period for at least 5 consecutive days, followed by administration of Compound $B^2$ alone for at least 5 consecutive days—in this case, the duration of time will be at least 10 consecutive days; suitably, during the course of treatment, both compounds will be administered within a specified period for at least 7 consecutive days, followed by administration of Compound $B^2$ alone for at least 2 consecutive days—in this case, the duration of time will be at least 9 consecutive days; suitably, during the course of treatment, both compounds will be administered within a specified period for at least 14 consecutive days, followed by administration of Compound $B^2$ alone for at least 7 consecutive days—in this case, the duration of time will be at least 21 consecutive days; suitably, during the course of treatment, both compounds will be administered within a specified period for at least 30 consecutive days, followed by administration of Compound $B^2$ alone for at least 7 consecutive days—in this case, the duration of time will be at least 37 consecutive days. Suitably, during the course of treatment, both compounds will be administered within a specified period for from 1 to 3 consecutive days, followed by administration of Compound $B^2$ alone for from 3 to 7 consecutive days. Suitably, during the course of treatment, both compounds will be administered within a specified period for from 3 to 6 consecutive days, followed by administration of Compound $B^2$ alone for from 1 to 4 consecutive days. Suitably, during the course of treatment, both compounds will be administered within a specified period for 5 consecutive days, followed by administration of Compound $B^2$ alone for 2 consecutive days. Suitably, during the course of treatment, both compounds will be administered within a specified period for 2 consecutive days, followed by administration of Compound $B^2$ alone for from 3 to 7 consecutive days.

Further regarding "specified period" administration:

Suitably, during the course of treatment, Compound $A^2$ and Compound $B^2$ will be administered within a specified period for from 1 to 3 days over a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for from 1 to 3 days over a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 3 days over a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 3 days over a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 2 days over a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 2 days over a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 1 day during a 7 day period, and during the other days of the 7 day period Compound $A^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for 1 day during a 7 day period, and during the other days of the 7 day period Compound $B^2$ will be administered alone. Suitably, this 7 day protocol is repeated for 2 cycles or for 14 days; suitably for 4 cycles or 28 days; suitably for continuous administration.

Suitably, during the course of treatment, Compound $A^2$ and Compound $B^2$ will be administered within a specified period for from 1 to 5 days over a 14 day period, and during the other days of the 14 day period Compound $A^2$ will be administered alone.

Suitably, this 14 day protocol is repeated for 2 cycles or for 28 days; suitably for continuous administration.

Suitably, during the course of treatment, Compound $A^2$ and Compound $B^2$ will be administered within a specified period for from 1 to 5 days over a 14 day period, and during the other days of the 14 day period Compound $B^2$ will be administered alone.

Suitably, this 14 day protocol is repeated for 2 cycles or for 28 days; suitably for continuous administration.

Suitably, if the compounds are not administered during a "specified period", they are administered sequentially. By the term "sequential administration", and derivates thereof, as used herein is meant that one of Compound $A^2$ and Compound $B^2$ is administered for two or more consecutive days and the other of Compound $A^2$ and Compound $B^2$ is subsequently administered for two or more consecutive days. Also, contemplated herein is a drug holiday utilized between the sequential administration of one of Compound $A^2$ and Compound $B^2$ and the other of Compound $A^2$ and Compound $B^2$. As used herein, a drug holiday is a period of days after the sequential administration of one of Compound $A^2$ and Compound $B^2$ and before the administration of the other of Compound $A^2$ and Compound $B^2$ where neither Compound $A^2$ nor Compound $B^2$ is administered. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Suitably, if the compounds are not administered during a "specified period", they are administered sequentially. By the term "sequential administration", and derivates thereof, as used herein is meant that one of Compound $A^2$ and Compound $B^2$ is administered once a day for one or more consecutive days and the other of Compound $A^2$ and Compound $B^2$ is subsequently administered once a day for one or more consecutive days. Also, contemplated herein is a drug holiday utilized between the sequential administration of one of Compound $A^2$ and Compound $B^2$ and the other of Compound $A^2$ and Compound $B^2$. As used herein, a drug holiday is a period of days after the sequential administration of one of Compound $A^2$ and Compound $B^2$ and before the administration of the other of Compound $A^2$ and Compound $B^2$ where neither Compound $A^2$ nor Compound $B^2$ is administered. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Regarding sequential administration:

Suitably, one of Compound $A^2$ and Compound $B^2$ is administered for from 2 to 30 consecutive days, followed by an optional drug holiday, followed by administration of the other of Compound $A^2$ and Compound $B^2$ for from 2 to 30 consecutive days. Suitably, one of Compound $A^2$ and Compound $B^2$ is administered for from 2 to 21 consecutive days, followed by an optional drug holiday, followed by administration of the other of Compound $A^2$ and Compound $B^2$ for from 2 to 21 consecutive days. Suitably, one of Compound $A^2$ and Compound $B^2$ is administered for from 2 to 14 consecutive days, followed by a drug holiday of from 1 to 14 days, followed by administration of the other of Compound $A^2$ and Compound $B^2$ for from 2 to 14 consecutive days. Suitably, one of Compound $A^2$ and Compound $B^2$ is administered for from 3 to 7 consecutive days, followed by a drug holiday of from 3 to 10 days, followed by administration of the other of Compound $A^2$ and Compound $B^2$ for from 3 to 7 consecutive days.

Suitably, one of Compound $A^2$ and Compound $B^2$ is administered for from 1 to 30 consecutive days, followed by an optional drug holiday, followed by administration of the other of Compound $A^2$ and Compound $B^2$ for from 1 to 30 consecutive days. Suitably, one of Compound $A^2$ and Compound $B^2$ is administered for from 1 to 21 consecutive days, followed by an optional drug holiday, followed by administration of the other of Compound $A^2$ and Compound $B^2$ for from 1 to 21 consecutive days. Suitably, one of Compound $A^2$ and Compound $B^2$ is administered for from 1 to 14 consecutive days, followed by a drug holiday of from 1 to 14 days, followed by administration of the other of Compound $A^2$ and Compound $B^2$ for from 1 to 14 consecutive days. Suitably, one of Compound $A^2$ and Compound $B^2$ is administered for from 2 to 7 consecutive days, followed by a drug holiday of from 2 to 10 days, followed by administration of the other of Compound $A^2$ and Compound $B^2$ for from 2 to 7 consecutive days.

Suitably, Compound $B^2$ will be administered first in the sequence, followed by an optional drug holiday, followed by administration of Compound $A^2$. Suitably, Compound $B^2$ is administered for from 3 to 21 consecutive days, followed by an optional drug holiday, followed by administration of Compound $A^2$ for from 3 to 21 consecutive days. Suitably, Compound $B^2$ is administered for from 3 to 21 consecutive days, followed by a drug holiday of from 1 to 14 days, followed by administration of Compound $A^2$ for from 3 to 21 consecutive days. Suitably, Compound $B^2$ is administered for from 3 to 21 consecutive days, followed by a drug holiday of from 3 to 14 days, followed by administration of Compound $A^2$ for from 3 to 21 consecutive days. Suitably, Compound $B^2$ is administered for 21 consecutive days, followed by an optional drug holiday, followed by administration of Compound $A^2$ for 14 consecutive days. Suitably, Compound $B^2$ is administered for 14 consecutive days, followed by a drug holiday of from 1 to 14 days, followed by administration of Compound $A^2$ for 14 consecutive days. Suitably, Compound $B^2$ is administered for 7 consecutive days, followed by a drug holiday of from 3 to 10 days, followed by administration of Compound $A^2$ for 7 consecutive days. Suitably, Compound $B^2$ is administered for 3 consecutive days, followed by a drug holiday of from 3 to 14 days, followed by administration of Compound $A^2$ for 7 consecutive days. Suitably, Compound $B^2$ is administered for 3 consecutive days, followed by a drug holiday of from 3 to 10 days, followed by administration of Compound $A^2$ for 3 consecutive days.

Suitably, Compound $B^2$ will be administered first in the sequence, followed by an optional drug holiday, followed by administration of Compound $A^2$. Suitably, Compound $B^2$ is administered for from 1 to 21 consecutive days, followed by an optional drug holiday, followed by administration of Compound $A^2$ for from 1 to 21 consecutive days. Suitably, Compound $B^2$ is administered for from 3 to 21 consecutive days, followed by a drug holiday of from 1 to 14 days, followed by administration of Compound $A^2$ for from 3 to 21 consecutive days. Suitably, Compound $B^2$ is administered for from 3 to 21 consecutive days, followed by a drug holiday of from 3 to 14 days, followed by administration of Compound $A^2$ for from 3 to 21 consecutive days. Suitably, Compound $B^2$ is administered for 21 consecutive days, followed by an optional drug holiday, followed by administration of Compound $A^2$ for 14 consecutive days. Suitably, Compound $B^2$ is administered for 14 consecutive days, followed by a drug holiday of from 1 to 14 days, followed by administration of Compound $A^2$ for 14 consecutive days. Suitably, Compound $B^2$ is administered for 7 consecutive days, followed by a drug holiday of from 3 to 10 days, followed by administration of Compound $A^2$ for 7 consecutive days. Suitably, Compound $B^2$ is administered for 3 consecutive days, followed by a drug holiday of from 3 to 14 days, followed by administration of Compound $A^2$ for 7 consecutive days. Suitably, Compound $B^2$ is administered for 3 consecutive days, followed by a drug holiday of from 3 to 10 days, followed by administration of Compound $A^2$ for 3 consecutive days.

Suitably, Compound $A^2$ will be administered first in the sequence, followed by an optional drug holiday, followed by administration of Compound $B^2$. Suitably, Compound $A^2$ is administered for from 3 to 21 consecutive days, followed by an optional drug holiday, followed by administration of Compound $B^2$ for from 3 to 21 consecutive days. Suitably, Compound $A^2$ is administered for from 3 to 21 consecutive days, followed by a drug holiday of from 1 to 14 days, followed by administration of Compound $B^2$ for from 3 to 21 consecutive days. Suitably, Compound $A^2$ is administered for from 3 to 21 consecutive days, followed by a drug holiday of from 3 to 14 days, followed by administration of Compound $B^2$ for from 3 to 21 consecutive days. Suitably, Compound $A^2$ is administered for 21 consecutive days, followed by an optional drug holiday, followed by administration of Compound $B^2$ for 14 consecutive days. Suitably, Compound $A^2$ is administered for 14 consecutive days, followed by a drug holiday of from 1 to 14 days, followed by administration of Compound $B^2$ for 14 consecutive days. Suitably, Compound $A^2$ is administered for 7 consecutive days, followed by a drug holiday of from 3 to 10 days, followed by administration of Compound $B^2$ for 7 consecutive days. Suitably, Compound $A^2$ is administered for 3 consecutive days, followed by a drug holiday of from 3 to 14 days, followed by administration of Compound $B^2$ for 7 consecutive days. Suitably, Compound $A^2$ is administered for 3 consecutive days, followed by a drug holiday of from 3 to 10 days, followed by administration of Compound $B^2$ for 3 consecutive days.

Suitably, Compound $A^2$ will be administered first in the sequence, followed by an optional drug holiday, followed by administration of Compound $B^2$. Suitably, Compound $A^2$ is administered for from 1 to 21 consecutive days, followed by an optional drug holiday, followed by administration of Compound $B^2$ for from 1 to 21 consecutive days. Suitably, Compound $A^2$ is administered for from 3 to 21 consecutive days, followed by a drug holiday of from 1 to 14 days, followed by administration of Compound $B^2$ for from 3 to 21 consecutive days. Suitably, Compound $A^2$ is administered for from 3 to 21 consecutive days, followed by a drug holiday of from 3 to 14 days, followed by administration of Compound $B^2$ for from 3 to 21 consecutive days. Suitably, Compound $A^2$ is administered for 21 consecutive days, followed by an optional drug holiday, followed by administration of Compound $B^2$ for 14 consecutive days. Suitably, Compound $A^2$ is administered for 14 consecutive days, followed by a drug holiday of from 1 to 14 days, followed by administration of Compound $B^2$ for 14 consecutive days. Suitably, Compound $A^2$ is administered for 7 consecutive days, followed by a drug holiday of from 3 to 10 days, followed by administration of Compound $B^2$ for 7 consecutive days. Suitably, Compound $A^2$ is administered for 3 consecutive days, followed by a drug holiday of from 3 to 14 days, followed by administration of Compound $B^2$ for 7 consecutive days. Suitably, Compound $A^2$ is administered for 3 consecutive days, followed by a drug holiday of from 3 to 10 days, followed by administration of Compound $B^2$ for 3 consecutive days. Suitably, Compound $A^2$ is administered for 7 consecutive days, followed by administration of Compound $B^2$ for 1 day. Suitably, Compound $A^2$ is administered for 6 consecutive days, followed by administration of Compound $B^2$ for 1 day. Suitably, Compound $B^2$ is administered for 1 day, followed by administration of Compound $A^2$ for 7 consecutive days. Suitably, Compound $B^2$ is administered for 1 day, followed by administration of Compound $A^2$ for 6 consecutive days.

It is understood that a "specified period" administration and a "sequential" administration can be followed by repeat dosing or can be followed by an alternate dosing protocol, and a drug holiday may precede the repeat dosing or alternate dosing protocol.

Suitably, the amount of Compound $A^2$ administered as part of the combination according to the present invention will be an amount selected from about 10 mg to about 300 mg; suitably, the amount will be selected from about 30 mg to about 280 mg; suitably, the amount will be selected from about 40 mg to about 260 mg; suitably, the amount will be selected from about 60 mg to about 240 mg; suitably, the amount will be selected from about 80 mg to about 220 mg; suitably, the amount will be selected from about 90 mg to about 210 mg; suitably, the amount will be selected from about 100 mg to about 200 mg, suitably, the amount will be selected from about 110 mg to about 190 mg, suitably, the amount will be selected from about 120 mg to about 180 mg, suitably, the amount will be selected from about 130 mg to about 170 mg, suitably, the amount will be selected from about 140 mg to about 160 mg, suitably, the amount will be 150 mg. Accordingly, the amount of Compound $A^2$ administered as part of the combination according to the present invention will be an amount selected from about 10 mg to about 300 mg. For example, the amount of Compound $A^2$ administered as part of the combination according to the present invention is suitably selected from 10 mg, 20 mg, 30 mg, 40 mg, 50 mg, 60 mg, 70 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg and 300 mg. Suitably, the selected amount of Compound $A^2$ is administered from 1 to 4 times a day. Suitably, the selected amount of Compound $A^2$ is administered twice a day. Suitably, the selected amount of Compound $A^2$ is administered once a day. Suitably, the administration of Compound $A^2$ will begin as a loading dose. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading does will be administered from 1 to 7 days; suitably from 1 to 5 days; suitably from 1 to 3 days; suitably for 1 day; suitably for 2 days; suitably for 3 days, followed by a maintenance dosing protocol.

Suitably, the amount of Compound $B^2$ administered as part of the combination according to the present invention will be an amount selected from about 5 mg to about 500 mg; suitably, the amount will be selected from about 25 mg to about 400 mg; suitably, the amount will be selected from about 30 mg to about 375 mg; suitably, the amount will be selected from about 35 mg to about 350 mg; suitably, the amount will be selected from about 40 mg to about 300 mg; suitably, the amount will be selected from about 45 mg to about 275 mg; suitably, the amount will be selected from about 50 mg to about 250 mg; suitably, the amount will be selected from about 55 mg to about 225 mg; suitably, the amount will be selected from about 60 mg to about 200 mg; suitably, the amount will be selected from about 65 mg to about 175 mg; suitably, the amount will be selected from about 70 mg to about 150 mg; suitably, the amount will be selected from about 50 mg to about 300 mg; suitably, the amount will be selected from about 75 mg to about 150 mg; suitably, the amount will be about 100 mg. Accordingly, the amount of Compound $B^2$ administered as part of the combination according to the present invention will be an amount selected from about 5 mg to about 500 mg. For example, the amount of Compound $B^2$ administered as part of the combination according to the present invention can be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 175 mg, 200 mg, 225 mg, 250 mg, 275 mg, 300 mg, 325 mg, 350 mg, 375 mg, 400 mg, 425 mg, 450 mg, 475 mg or 500 mg. Suitably, the selected amount of Compound $B^2$ is administered twice a day. Suitably, the selected amount of Compound $B^2$ is administered once a day. Suitably, the administration of Compound $A^2$ will begin as a loading dose. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading does will be administered from 1 to 7 days; suitably from 1 to 5 days; suitably from 1 to 3 days; suitably for 1 day; suitably for 2 days; suitably for 3 days, followed by a maintenance dosing protocol.

Suitably, the amount of Compound $B^2$ administered as part of the combination according to the present invention will be an amount selected from about 75 mg to about 1,000 mg; suitably, the amount will be selected from about 100 mg to about 900 mg; suitably, the amount will be selected from about 150 mg to about 850 mg; suitably, the amount will be selected from about 200 mg to about 800 mg; suitably, the amount will be selected from about 250 mg to about 750 mg; suitably, the amount will be selected from about 300 mg to about 6000 mg; suitably, the amount will be about 450 mg. Accordingly, the amount of Compound $B^2$ administered as part of the combination according to the present invention will be an amount selected from about 75 mg to about 1,000 mg. For example, the amount of Compound $B^2$ administered as part of the combination according to the present invention can be 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg or 1,000 mg. Suitably, the selected amount of Compound $B^2$ is administered twice a day. Suitably, the selected amount of Compound $B^2$ is administered once a day.

As used herein, all amounts specified for Compound $A^2$ and Compound $B^2$ are indicated as the administered amount of free or unsalted and unsolvated compound per dose.

The method of the present invention may also be employed with other therapeutic methods of cancer treatment.

While it is possible that, for use in therapy, therapeutically effective amounts of the combinations of the present invention may be administered as the raw chemical, it is preferable to present the combinations as a pharmaceutical composition or compositions. Accordingly, the invention further provides pharmaceutical compositions, which include Compound $A^2$ and/or Compound $B^2$, and one or more pharmaceutically acceptable carriers. The combinations of the present invention are as described above. The carrier(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical formulation including admixing Compound $A^2$ and/or Compound $B^2$ with one or more pharmaceutically acceptable carriers. As indicated above, such elements of the pharmaceutical combination utilized may be presented in separate pharmaceutical compositions or formulated together in one pharmaceutical formulation.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage formulations are those containing a daily dose or subdose, or an appropriate fraction thereof, of an active ingredient. Furthermore, such pharmaceutical formulations may be prepared by any of the methods well known in the pharmacy art.

Compound $A^2$ and Compound $B^2$ may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that Compound $A^2$ and Compound $B^2$ may be compounded together in a pharmaceutical composition/formulation.

The compounds or combinations of the current invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include a prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will suitably be in the form of a syrup, elixir, emulsion, soft gelatin capsule, sterile injectable liquid such as an ampoule, or an aqueous or nonaqueous liquid suspension.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

It should be understood that in addition to the ingredients mentioned above, the formulations may include other agents conventional in the art having regard to the type of formulation in question, for example those suitable for oral administration may include flavoring agents.

As indicated, therapeutically effective amounts of the combinations of the invention (Compound $A^2$ in combination with Compound $B^2$) are administered to a human. Typically, the therapeutically effective amount of the administered agents of the present invention will depend upon a number of factors including, for example, the age and weight of the subject, the precise condition requiring treatment, the severity of the condition, the nature of the formulation, and the route of administration. Ultimately, the therapeutically effective amount will be at the discretion of the attendant physician.

The combinations of the present invention are tested for efficacy, advantageous and synergistic properties according to known procedures.

Suitably, the combinations of the invention are tested for efficacy, advantageous and synergistic properties generally according to the following combination cell proliferation assays. Cells are plated in 384-well plates at 500 cells/well in culture media appropriate for each cell type, supplemented with 10% FBS and 1% penicillin/streptomycin, and incubated overnight at 37° C., 5% $CO_2$. Cells are treated in a grid manner with dilution of Compound $A^2$ (20 dilutions, including no compound, of 2-fold dilutions starting from 1-20 µM depending on combination) from left to right on 384-well plate and also treated with Compound $B^2$ (20 dilutions, including no compound, of 2-fold dilutions starting from 1-20 µM depending on combination) from top to bottom on 384-well plate and incubated as above for a further 72 hours. In some instances compounds are added in a staggered manner and incubation time can be extended up to 7 days. Cell growth is measured using CellTiter-Glo® reagent according to the manufacturer's protocol and signals are read on a PerkinElmer EnVision™ reader set for luminescence mode with a 0.5-second read. Data are analyzed as described below.

Results are expressed as a percentage of the t=0 value and plotted against compound(s) concentration. The t=0 value is normalized to 100% and represents the number of cells present at the time of compound addition. The cellular response is determined for each compound and/or compound combination using a 4- or 6-parameter curve fit of cell viability against concentration using the IDBS XLfit plug-in for Microsoft Excel software and determining the concentration required for 50% inhibition of cell growth (gIC$_{50}$). Background correction is made by subtraction of values from wells containing no cells. For each drug combination a Combination Index (CI), Excess Over Highest Single Agent (EOHSA) and Excess Over Bliss (EOBliss) are calculated according to known methods such as described in Chou and Talalay (1984) Advances in Enzyme Regulation, 22, 37 to 55; and Berenbaum, M C (1981) Adv. Cancer Research, 35, 269-335.

In Vitro Combination Studies of BRAF and AKT Inhibitors on Cancer Cells Lines from Multiple Origins Encoding Different Mutations within the MAPK and AKT/PI3K Pathways Drug combinations experiments were carried out in 384-well plates. Cell were plated in 384-well plates at 500 cells/well in culture media appropriate for each cell type, supplemented with 10% FBS and 1% penicillin/streptomycin, and incubated overnight at 37° C., 5% CO$_2$. Sixteen concentrations of 2 folds dilution of each drug were tested in matrix for cell growth inhibition. Concentrations tested for the Compound A (BRAF compound) and Compound B (AKT compound) were 10 µM-0.3 nM. Cells were treated with compound combination and incubated at 37° C. for 72 hours. Cell growth was measured using CellTiter-Glo® reagent according to the manufacturer's protocol and signals are read on a PerkinElmer EnVision™ reader set for luminescence mode with a 0.5-second read. Results are expressed as a percentage inhibition compared to DMSO treated cells and background correction was made by subtraction of values from wells containing no cells.

The response (percent inhibition compared to untreated samples and normalized to media alone) of compound "A" at "a" concentration (Ra) and that of compound "B" at "b" concentration (Rb) is compared to response of the mixture of compounds "A" and "B" at concentrations "a" and "b" respectively (Rab). The equation for EOHSA is:

Rab>10% of the higher value among Ra and Rb=additive
Rab<−10% of the higher value among Ra and Rb=antagonism Using this formula, if Rab is greater by 10% or more than the highest value between Ra and Rb the drug combination is additive. If Rab is smaller by 10% or more than the highest value between Ra and Rb the drug combination is antagonistic.

The number of combinations in the 16×16 matrix responding in an additive manner to the combination treatment were enumerated and summarized in Table 1. On this table we assigned a combination on a given cell line to be beneficial (gray square) if more than 20% (51 combination out of 256 tested) of combinations tested showed additivity as defined by a value greater than 10% Excess Over the Highest Single Agent (10% EOHSA).

TABLE 1

Combination effect of AKT and BRAF inhibitors on multiple cancer cell lines.

| Origin | Cell Lines | MAPK | PI3K/PTEN | # of drug combinations w EOHSA | % |
|---|---|---|---|---|---|
| Skin | A375P | BRAF$^{V600E}$ | WT/WT | 48 | 19 |
| Colon | RKO | BRAF$^{V600E}$ | mut/WT | 123 | 48 |
| Skin | A101D | BRAF$^{V600E}$ | WT/mut | 81 | 32 |
| Skin | SK-MEL-5 | BRAF$^{V600E}$ NRAS$^{G12V}$ | WT/inc | 92 | 36 |
| Lung | A-549 | KRAS$^{G12S}$ | WT/WT | 59 | 23 |
| Colon | LoVo | KRAS$^{G13D}$ | WT/WT | 70 | 27 |
| Colon | HCT116 | KRAS$^{G13D}$ | mut/WT | 60 | 23 |
| Skin | SK-MEL-2 | NRAS$^{Q61R}$ | WT/WT | 65 | 25 |
| Lung | H1299 | NRAS$^{Q61R}$ | WT/WT | 46 | 18 |
| Sarcoma | HT-1080 | NRAS$^{Q61K}$ | WT/WT | 59 | 23 |
| Breast | MDA-MB-231 | NRAS$^{Q61K}$ | WT/WT | 59 | 23 |

These data demonstrate that the combination of AKT and BRAF inhibitors is favorable on multiple cancer cell lines from multiple origins independent of the mutational status of key oncogenes within the MAPK or the AKT/PI3K pathways as multiple drug combinations (>20%) showed inhibitory activity >10% Excess Over Highest Single Agent (EOHSA).

In Vitro Cell Growth Inhibition by Compound A (BRAF Compound), Compound B (AKT Compound), and their Combination in Tumor Cell Lines Methods:

Cell Lines and Growth Conditions

Human colon tumor lines, Colo205, DLD1, HCC2998, HCT15, HCT8, HT29, KM-12, LS1034, LS174T, NCI-H508, RKO, SW1417, SW1463, SW480, SW837 and T84, and human melanoma line A375 were from ATCC. A375PF11 was derived from A375, 12R5-1, 12R5-3, 12R8-1, 12R8-3, 16R5-2, 16R6-3 and 16R6-4 are single cell clones derived from mixed populations of A375PF11 cells that were selected to grow in Compound A to concentrations of 1200 and 1600 nM. All lines were cultured in RPMI 1640 medium containing 10% fetal bovine serum (FBS).

Cell Growth Inhibition Assay and Combination Data Analysis.

All cells were cultured for a minimum of 72 hours prior to cell plating. Cells were assayed in a 96-well tissue culture plate (NUNC 136102) of RPMI medium containing 10% FBS for all cells at 1,000 cells per well. Approximately 24 hours after plating, cells were exposed to ten, three-fold serial dilutions of compound or the combination of the two agents at a constant molar to molar ratio of 1:10 Compound A to Compound B in RPMI media containing 10% FBS. Cells were incubated in the presence of compounds for 3 days. ATP levels were determined by adding Cell Titer Glo® (Promega) according to the manufacturer's protocol. Briefly, Cell Titer Glo® was added each plate, incubated for 30 minutes then luminescent signal was read on the SpectraMax L plate reader with a 0.5 sec integration time.

Inhibition of cell growth was estimated after treatment with compound or combination of compounds for three days and comparing the signal to cells treated with vehicle (DMSO). Cell growth was calculated relative to vehicle (DMSO) treated control wells. Concentration of compound that inhibits 50% of control cell growth ($IC_{50}$) was interpolated when y=50% of the vehicle control using nonlinear regression with the equation, $y=(A+(B-A)/(1+(C/x)^D)))$, where A is the minimum response ($y_{min}$), B is the maximum response ($y_{max}$), C is the inflection point of the curve ($EC_{50}$) and D is the Hill coefficient.

Combination effects on potency were evaluated using Combination Index (CI) which was calculated with the back-interpolated $IC_{50}$ values and the mutually non-exclusive equation derived by Chou and Talalay (1):

$$CI=Da/IC_{50}(a)+Db/IC_{50}(b)+(Da \times Db)/(IC_{50}(a) \times IC_{50}(b))$$

where $IC_{50}(a)$ is the $IC_{50}$ of Compound A; $IC_{50}(b)$ is the $IC_{50}$ for Compound B; Da is the concentration of Compound A in combination with Compound B that inhibited 50% of cell growth; and Db is the concentration of Compound B in combination with Compound A that inhibited 50% of cell growth. In general, a CI value <0.9, between 0.9 and 1.1, or >1.1 indicates synergy, additivity and antagonism, respectively. In general, the smaller the CI number, the greater is the strength of synergy.

The combination effects on the response scale were quantified by Excess Over Highest Single Agent (EOHSA) based on the concept of nonlinear blending as described in detail by Peterson and Novick (2007) and Peterson (2010) [(2;3) [Peterson and Novick, 2007; Peterson, 2010]. EOHSA values are defined as increases in improvement (here, in 'percentage points' (ppts) difference) produced by the combination over the best single agent at its component dose level for the combination. For single agent and combination treatments, cells were exposed to compounds at a fixed-dose-ratio, and dose response curves were fit to the experimental data and analyzed using regression models. At specified total dose levels of $IC_{50}$ along the dose response curve, the dose combination (corresponding to $IC_{50}$) was determined for making EOHSA statistical inferences. More specifically, for a combination drug experiment involving drug 1 at dose d1 and drug 2 at dose d2, (i.e., total dose equals d1+d2) is said to have a positive EOHSA if the mean response at the combination is better than the mean response to drug 1 at dose d1 or drug 2 at dose d2.

Results:

The effect of cell growth inhibition by a BRAF inhibitor Compound A, an AKT inhibitor Compound B and their combination was determined in a panel of human tumor cell lines. The mean $IC_{50}$s (from at least two independent experiments) and the combination effects at $IC_{50}$s are summarized in Table 2 with BRAF, KRAS and PIK3CA mutation status.

The four colon cell lines with BRAF V600E mutation displayed sensitivity to Compound A with IC50 values between 0.018 μM and 3.316 μM, and to Compound B with $IC_{50}$ values between 0.290 μM and 2.587 μM. The combination of Compound A and Compound B was highly synergistic with CI value of 0.16 in RKO cells with mutations of both BRAF V600E and PIK3CA H1047R, and moderately synergistic or additive in SW1417, Colo205 and HT29 lines. The other 12 colon lines without BRAF V600E mutation were insensitive to Compound A ($IC_{50}$s>5 μM). The combination of Compound A and Compound B showed enhanced cell growth inhibition demonstrated by the EOHSA values from 17 to 54 ppts in these lines.

For the melanoma tumor lines listed in Table 2, A375PF11 cells with BRAF V600E mutation were highly sensitive to Compound A ($IC_{50}$=0.063 μM), but insensitive to Compound B ($IC_{50}$>10 μM). The combination of Compound A and Compound B showed activity similar to Compound A alone in A375PF11 cells. The seven Compound A resistant clones (12R8-3, 12R8-1, 12R5-3, 16R5-2, 16R6-3, 16R6-4 and 12R5-1 derived from the A375PF11 melanoma cell line) were insensitive to Compound B with $IC_{50}$s≥7 μM. The combination of Compound A and Compound B showed enhanced cell growth inhibition at relatively higher concentrations (~1 μM) of both Compound A and Compound B.

Table 2. Cell growth inhibition by Compound A, Compound B and their combination in human tumor cell lines.

TABLE 2

| | | Mutation Status | | | Single Agent | | Compound A or B at 1:1 molar ratio | Combination Effects | |
|---|---|---|---|---|---|---|---|---|---|
| | | | | | IC50 values in micromolar (mean ± std) | | | | |
| | Cell Lines | BRAF | KRAS | PIK3CA | Compound A | Compound B | combination | CI | EOHSA |
| Colon | RKO | V600E | WT | H1047R | 3.136 ± 3.466 | 0.290 ± 0.070 | 0.038 ± 0.012 | 0.16 ± 0.02 | 26 ± 2 |
| | SW1417 | V600E | WT | WT | 0.101 ± 0.031 | 2.587 ± 1.757 | 0.065 ± 0.025 | 0.69 ± 0.03 | 4 ± 1 |
| | HT29 | V600E | WT | P449T | 0.028 ± 0.007 | 0.503 ± 0.073 | 0.023 ± 0.001 | 0.95 ± 0.27 | 2 ± 4 |
| | Colo205 | V600E | WT | WT | 0.018 ± 0.003 | 0.908 ± 0.605 | 0.017 ± 0.002 | 0.97 ± 0.01 | 2 ± 1 |
| | NCI-H508 | G596R | WT | E545K | >10 | 0.234 ± 0.247 | 0.103 ± 0.088 | N/A | 19 ± 11 |
| | HCT8 | WT | G13D | E545K | >10 | 0.527 ± 0.036 | 0.236 ± 0.036 | N/A | 15 ± 2 |
| | KM-12 | WT | WT | WT | >10 | 1.412 ± 0.961 | 0.503 ± 0.266 | N/A | 20 ± 9 |
| | HCT15 | WT | G13D | D549N, E545K | >10 | 4.205 ± 0.834 | 0.610 ± 0.039 | N/A | 38 ± 3 |
| | HCC2998 | WT | A146T | WT | >10 | 2.912 ± 1447 | 0.686 ± 0.043 | N/A | 21 ± 4 |
| | DLD1 | WT | G13D | E545K, D549N | >10 | >10 | 0.762 ± 0.083 | N/A | 32 ± 3 |
| | LS174T | WT | G12D | H1047R | >10 | 3.746 ± 0.945 | 0.946 ± 0.202 | N/A | 39 ± 11 |
| | SW480 | WT | G12C | WT | >10 | 5.625 ± 1.853 | 1.441 ± 1.022 | N/A | 26 ± 3 |
| | LS1034 | WT | A146T | WT | >10 | 6.393 ± 3.554 | 1.519 ± 0.524 | N/A | 17 ± 0 |
| | SW1463 | WT | G12C | WT | >10 | 5.230 ± 7.396 | 2.797 ± 2.174 | N/A | 54 ± 5 |
| | SW837 | WT | G12C | WT | 5.437 ± 7.689 | >10 | 3.582 ± 0.554 | N/A | 25 ± 14 |
| | T84 | WT | G13D | E542K | >10 | >10 | 5.121 ± 2.507 | N/A | 50 ± 0 |

TABLE 2-continued

| | | Mutation Status | | | Single Agent | | Compound A or B at 1:1 molar ratio | Combination Effects | |
|---|---|---|---|---|---|---|---|---|---|
| Cell Lines | | BRAF | KRAS | PIK3CA | Compound A | Compound B | combination | CI | EOHSA |
| Melanoma | F11 | BRAF_V600E | WT | NT | 0.063 ± 0.004 | >10 | 0.090 ± 0.021 | 1.443 ± 0.245 | −5 ± 4 |
| | 16R5-2 | BRAF_V600E | WT | NT | >10 | 7.050 ± 1.326 | 0.897 ± 0.071 | N/A | 32 ± 1 |
| | 16R6-4 | BRAF_V600E | WT | NT | >10 | >10 | 1.122 ± 0.083 | N/A | 41 ± 13 |
| | 12R5-1 | BRAF_V600E | WT | NT | >10 | >10 | 1.176 ± 0.014 | N/A | 65 ± 7 |
| | 12R5-3 | BRAF_V600E | WT | NT | >10 | >10 | 1.229 ± 0.394 | N/A | 44 ± 20 |
| | 12R8-3 | BRAF_V600E | WT | NT | >10 | >10 | 1.271 ± 0.142 | N/A | 55 ± 6 |
| | 12R8-1 | BRAF_V600E | WT | NT | >10 | >10 | 1.667 ± 0.125 | N/A | 45 ± 0 |
| | 16R6-3 | BRAF_V600E | WT | NT | >10 | >10 | 1.720 ± 0.300 | N/A | 42 ± 5 |

Table 2 Key:
$IC_{50}$: the concentration of Compound(s) or the concentration of Compound A in the presence of equal molar Compound B that reduces cell growth by 50%;
CI = Combination Index;
N/A = not applicable;
NT = not tested.
EOHSA: Excess over Highest Single Agent, measured as a percentage.
F11: A375PF11.

REFERENCE LIST (1) Chou T C, Talalay P. Quantitative analysis of dose-effect relationships: the combined effects of multiple drugs or enzyme inhibitors. Adv Enzyme Regul 1984; 22:27-55.
(2) Peterson J J, Novick S J. Nonlinear blending: a useful general concept for the assessment of combination drug synergy. J Recept Signal Transduct Res 2007; 27(2-3):125-46.
(3) Peterson J. A Review of Synergy Concepts of Nonlinear Blending and Dose-Reduction Profiles. Frontiers of Bioscience S2, 483-503. 2010.

Because the combinations of the present invention are active in the above assays they exhibit advantageous therapeutic utility in treating cancer.

Suitably, the present invention relates to a method for treating or lessening the severity of a cancer selected from: brain (gliomas), glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably, the present invention relates to a method for treating or lessening the severity of a cancer selected from: brain (gliomas), glioblastomas, astrocytomas, glioblastoma multiforme, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

Suitably the present invention relates to a method for treating or lessening the severity of pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

Suitably, the present invention relates to a method of treating or lessening the severity of a cancer that is either wild type or mutant for Raf and either wild type or mutant for PI3K/Pten. This includes patients wild type for both Raf and PI3K/PTEN, mutant for both Raf and PI3K/PTEN, mutant for Raf and wild type for PI3K/PTEN and wild type for Raf and mutant for PI3K/PTEN.

The term "wild type" as is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Included in the term mutant is Single Nucleotide Polymorphism (SNP) where a single base pair distinction exists in the sequence of a nucleic acid strand compared to the most prevalently found (wild type) nucleic acid strand.

Cancers that are either wild type or mutant for Raf and either wild type or mutant for PI3K/Pten are identified by known methods.

For example, wild type or mutant Raf or PI3K/PTEN tumor cells can be identified by DNA amplification and sequencing techniques, DNA and RNA detection techniques, including, but not limited to Northern and Southern blot, respectively, and/or various biochip and array technologies. Wild type and mutant polypeptides can be detected by a variety of techniques including, but not limited to immunodiagnostic techniques such as ELISA, Western blot or immunocyto chemistry. Suitably, Pyrophosphorolysis-activated polymerization (PAP) and/or PCR methods may be used. Liu, Q et al; Human Mutation 23:426-436 (2004).

This invention provides a combination comprising N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof.

This invention also provides for a combination comprising N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, for use in therapy.

This invention also provides for a combination comprising N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, for use in treating cancer.

This invention also provides a pharmaceutical composition comprising a combination of N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof.

This invention also provides a combination kit comprising N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof.

This invention also provides for the use of a combination comprising N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, in the manufacture of a medicament.

This invention also provides for the use of a combination comprising N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, in the manufacture of a medicament to treat cancer.

This invention also provides a method of treating cancer which comprises administering a combination of N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, to a subject in need thereof.

The following examples are intended for illustration only and are not intended to limit the scope of the invention in any way.

EXPERIMENTAL DETAILS

Example 1

Capsule Composition

An oral dosage form for administering a combination of the present invention is produced by filing a standard two piece hard gelatin capsule with the ingredients in the proportions shown in Table I, below.

TABLE I

| INGREDIENTS | AMOUNTS |
|---|---|
| N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate (the methanesulfonate salt of Compound A) | 100 mg |
| N-{(1S)-2-amino-1-[(3,4-difluorophenyl)methyl]ethyl}-5-chloro-4-(4-chloro-1-methyl-1H-pyrazol-5-yl)-2-furancarboxamide (Compound B) | 300 mg |
| Mannitol | 250 mg |
| Talc | 125 mg |
| Magnesium Stearate | 8 mg |

Example 2

Capsule Composition

An oral dosage form for administering one of the compounds of the present invention is produced by filing a standard two piece hard gelatin capsule with the ingredients in the proportions shown in Table II, below.

TABLE II

| INGREDIENTS | AMOUNTS |
|---|---|
| N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate (the methanesulfonate salt of Compound A) | 100 mg |
| Mannitol | 55 mg |
| Talc | 16 mg |
| Magnesium Stearate | 4 mg |

Example 3

Capsule Composition

An oral dosage form for administering one of the compounds of the present invention is produced by filing a standard two piece hard gelatin capsule with the ingredients in the proportions shown in Table III, below.

TABLE III

| INGREDIENTS | AMOUNTS |
|---|---|
| N-{(1S)-2-amino-1-[(3,4-difluorophenyl)methyl]ethyl}-5-chloro-4-(4-chloro-1-methyl-1H-pyrazol-5-yl)-2-furancarboxamide (Compound B) | 300 mg |

TABLE III-continued

| INGREDIENTS | AMOUNTS |
| --- | --- |
| Mannitol | 250 mg |
| Talc | 125 mg |
| Magnesium Stearate | 8 mg |

Example 4

Tablet Composition

The sucrose, microcrystalline cellulose and the compounds of the invented combination, as shown in Table IV below, are mixed and granulated in the proportions shown with a 10% gelatin solution. The wet granules are screened, dried, mixed with the starch, talc and stearic acid, then screened and compressed into a tablet.

TABLE IV

| INGREDIENTS | AMOUNTS |
| --- | --- |
| N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate (the methanesulfonate salt of Compound A) | 100 mg |
| N-{(1S)-2-amino-1-[(3,4-difluorophenyl)methyl]ethyl}-5-chloro-4-(4-chloro-1-methyl-1H-pyrazol-5-yl)-2-furancarboxamide (Compound B) | 300 mg |
| Microcrystalline cellulose | 300 mg |
| sucrose | 10 mg |
| starch | 40 mg |
| talc | 20 mg |
| stearic acid | 5 mg |

Example 5

Tablet Composition

The sucrose, microcrystalline cellulose and one of the compounds of the invented combination, as shown in Table V below, are mixed and granulated in the proportions shown with a 10% gelatin solution. The wet granules are screened, dried, mixed with the starch, talc and stearic acid, then screened and compressed into a tablet.

TABLE V

| INGREDIENTS | AMOUNTS |
| --- | --- |
| N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate (the methanesulfonate salt of Compound A) | 100 mg |
| Microcrystalline cellulose | 30 mg |
| sucrose | 4 mg |
| starch | 2 mg |
| talc | 1 mg |
| stearic acid | 0.5 mg |

Example 6

Tablet Composition

The sucrose, microcrystalline cellulose and one of the compounds of the invented combination, as shown in Table VI below, are mixed and granulated in the proportions shown with a 10% gelatin solution. The wet granules are screened, dried, mixed with the starch, talc and stearic acid, then screened and compressed into a tablet.

TABLE VI

| INGREDIENTS | AMOUNTS |
| --- | --- |
| N-{(1S)-2-amino-1-[(3,4-difluorophenyl)methyl]ethyl}-5-chloro-4-(4-chloro-1-methyl-1H-pyrazol-5-yl)-2-furancarboxamide (Compound B) | 300 mg |
| Microcrystalline cellulose | 300 mg |
| sucrose | 40 mg |
| starch | 20 mg |
| talc | 10 mg |
| stearic acid | 5 mg |

While the preferred embodiments of the invention are illustrated by the above, it is to be understood that the invention is not limited to the precise instructions herein disclosed and that the right to all modifications coming within the scope of the following claims is reserved.

We claim:

1. A method of treating a cancer selected from melanoma, breast, colon, lung, and sarcoma in a human in need thereof which comprises the in vivo administration of a therapeutically effective amount of a combination of N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, to such human,
   wherein the combination is administered within a specified period, and
   wherein the combination is administered for a duration of time.

2. A method according to claim 1 wherein the amount of N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, is selected from about 70 mg to about 260 mg, and that amount is administered twice per day, and the amount of N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, is selected from about 10 mg to about 300 mg, and that amount is administered once per day.

3. A method according to claim 1 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within 12 hours of each other for from 1 to 3 consecutive days followed by administration of N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof for from 3 to 7 consecutive days, optionally followed by one or more cycles of repeat dosing.

4. A method of treating a cancer selected from melanoma, breast, colon, lung, and sarcoma that is either wild type or mutant for Raf and either wild type or mutant for PI3K/PTEN in a human in need thereof which comprises the in vivo administration of a therapeutically effective amount of a combination of N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, to such human,
wherein the combination is administered within a specified period, and
wherein the combination is administered for a duration of time.

5. A method according to claim 4 wherein the amount of N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, is selected from about 70 mg to about 260 mg, and that amount is administered twice per day, and the amount of N-{(1S)-2-amino-1-[(3,4-difluorophenyl)methyl]ethyl}-5-chloro-4-(4-chloro-1-methyl-1H-pyrazol -5-yl)-2-furancarboxamide, or a pharmaceutically acceptable salt thereof, is selected from about 10 mg to about 300 mg, and that amount is administered once per day.

6. A method according to claim 2 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within 12 hours of each other for 2 days over a 7 day period, and during the other days of the 7 day period N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, is administered alone, optionally followed by one or more cycles of repeat dosing.

7. A method according to claim 3 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within hours of each other for 2 consecutive days followed by administration of N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, for from 4 to 6 consecutive days, optionally followed by one or more cycles of repeat dosing.

8. A method according to claim 5 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within 12 hours of each other for 2 days over a 7 day period, and during the other days of the 7 day period N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, is administered alone, optionally followed by one or more cycles of repeat dosing.

9. A method according to claim 2 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within 12 hours of each other for at least 5 consecutive days.

10. A method according to claim 5 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within 12 hours of each other for 5 consecutive days followed by administration of N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, for 2 consecutive days, optionally followed by one or more cycles of repeat dosing.

11. A method according to claim 5 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within 12 hours of each other for 5 days over a 14 day period, and during the other days of the 14 day period N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, optionally followed by one or more cycles of repeat dosing.

12. A method according to claim 5 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within 12 hours of each other for 2 days over a 7 day period, and during the other days of the 7 day period N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, is administered alone, optionally followed by one or more cycles of repeat dosing.

13. A method according to claim 5 wherein N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, are administered within hours of each other for 5 days over a 14 day period, and during the other days of the 14 day period N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, is administered alone, optionally followed by one or more cycles of repeat dosing.

14. A method according to claim 5 wherein the compound N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, is first administered in a loading dose for from 1 to 3 days followed by maintenance dose administration of the compound.

15. A method according to claim 5 wherein the compound N-{(1S)-2-amino-1-[(3,4-difluorophenyl)methyl]ethyl}-5-chloro-4-(4-chloro-1-methyl-1H-pyrazol-5-yl)-2-furancarboxamide, or a pharmaceutically acceptable salt thereof, is first administered in a loading dose for from 1 to 3 days followed by maintenance dose administration of the compound.

\* \* \* \* \*